United States Patent [19]

Dietz

[11] Patent Number: 4,747,842

[45] Date of Patent: May 31, 1988

[54] ARTICLE FOR APPLYING STYPTIC TO A DOG'S BLEEDING NAIL

[76] Inventor: David Dietz, 2084 Flatbush Ave., Brooklyn, N.Y. 11234

[21] Appl. No.: 65,267

[22] Filed: Jun. 22, 1987

[51] Int. Cl.⁴ .............................................. A61M 35/00

[52] U.S. Cl. .............................................. 604/309; 119/1

[58] Field of Search ........................ 604/309; 119/1, 83

[56] References Cited

U.S. PATENT DOCUMENTS

| | | | |
|---|---|---|---|
| 2,290,886 | 7/1942 | Lenz | 604/309 |
| 3,275,132 | 9/1966 | Hultgren | 604/309 X |
| 3,948,265 | 4/1976 | Alani | 604/309 |

*Primary Examiner*—John D. Yasko

*Attorney, Agent, or Firm*—Cohen, Pontani & Lieberman

[57] ABSTRACT

An article for applying styptic powder to a dog's bleeding nail includes a body in which a cavity extending substantially vertically from the top of the body into the interior thereof is defined. The cavity has at least a portion of predetermined depth—being the maximum extension of the cavity from the top of the body to the cavity bottom—which substantially corresponds to the length of a dog's manicured nail. A quantity of styptic powder is contained in the cavity and, when a dog's bleeding nail is fully inserted into the cavity so that the nail end contacts the cavity bottom portion of predetermined depth, the styptic powder is properly applied to the nail and soiling of the paws and coat and other body portions of the dog with styptic powder is readily and reliably avoided.

3 Claims, 1 Drawing Sheet

ARTICLE FOR APPLYING STYPTIC TO A DOG'S BLEEDING NAIL

FIELD OF THE INVENTION

The invention relates generally to accessories used in connection with the grooming of pets, such as dogs. More particularly, the invention is directed to an article for facilitating the application of styptic to the bleeding nail of a dog in an easy, effective and neat manner while avoiding soiling the paws and other body portions and coat of the dog with styptic material.

BACKGROUND OF THE INVENTION

Of particular importance to the many millions of individuals who own pets, such cats and dogs, is maintaining the proper appearance of the animal. Not unexpectedly, an entire industry has evolved around the grooming of pets, even those not intended to be placed on formal public display as in shows or contests and the like. The grooming of pets commonly includes such steps as washing, combing, brushing, and cutting the animal's coat, and the manicuring of the animal's nails.

In the manicuring of animal nails—and particularly, although not exclusively, with respect to dogs—the nails are clipped to a length which, within a relatively small range, is fairly standard. The ends of the nails may thereafter be filed or otherwise burnished to smooth the nail ends and remove sharp edges or projecting portions that might otherwise undesirably engage or snag fabrics and materials forming, for example, carpets, draperies and clothing.

As is well known, a small vein runs longitudinally through each nail of animals such as dogs and it is not uncommon, in the course of manicuring a dog's nails, that one or more of the nails begins to bleed from or in the area of the cut nail end. In order to control and stop such bleeding, a styptic agent or material—typically in the form of a powder, but less often in the form of a bar of styptic material which is rubbed over the affected area—is applied to the nail. As one might expect, however, it is most unusual for the dog whose nails are being manicured to remain calm, let alone silent, through this entire procedure. In particular, the process of applying the styptic powder to the ends of the bleeding nails of a squirming or otherwise struggling dog almost always results in soiling of the dog's paws and other portions of the animal's body and coat as the styptic powder is splattered into the air and onto the animal's, and the handler's, bodies. This effect is directly contrary to the very purpose for which the dog is undergoing grooming—namely, to improve the attractiveness of the animal's appearance so that the owner and others may observe the dog as exemplary of its breed.

SUMMARY OF THE INVENTION

It is accordingly the desideratum of the invention to provide an article for facilitating the cessation of bleeding from the nails of animals during the manicuring of the animal's nails. It is a particular object to provide such an article for facilitating the application of styptic powder to the animal's bleeding nails while avoiding the usual soiling of the paws and other body portions and coat of the animal with the styptic powder.

It is another object of the invention to provide such an article for retaining a quantity of styptic powder in a relatively enclosed area which is readily accessible for receiving the animal's nail to which the styptic powder is to be applied.

It is a further object of the invention to provide such an article wherein an animal's bleeding nail is insertable into the relatively enclosed area containing the styptic powder to an extent appropriate for applying the styptic powder only to the bleeding nail.

It is still another object of the invention to provide such an article in which the relatively enclosed area containing the styptic powder is so configured that the bleeding nail is insertable into said area only to that extent required to properly apply the styptic powder to the nail Further objects, features and advantages of the present invention will be more fully appreciated by reference to the following detailed description of a presently preferred, but nonetheless illustrative, embodiment in accordance with the present invention when taken in conjunction with the accompanying drawing.

BRIEF DESCRIPTION OF THE DRAWING

In the drawing, wherein similar reference characters denote similar elements throughout the several views.

DETAILED DESCRIPTION OF THE PREFERRED EMBODIMENT

Figure 1:
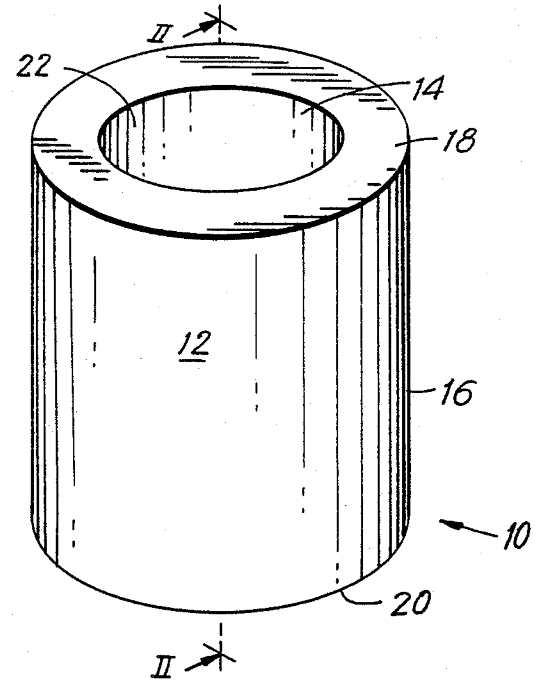
FIG. 1 is an elevated perspective view of an article for containing a styptic powder and for receiving the bleeding nail of an animal in accordance with the invention.

The present invention is generally directed to an accessory for use in the grooming of animals, typically pets such as dogs and cats. As such, the invention provides a receptacle-like article for containing a quantity of styptic material, in powdered form, and into which an animal's bleeding nail is insertable to a predetermined depth for neatly and appropriately applying styptic powder to the bleeding nail and thereby facilitating the cessation of bleeding from the nail end. It should at the outset be understood that although the article of the invention, as herein disclosed, is specifically intended and disclosed for use with dogs, the invention is equally applicable in respect of a variety of other animals such, for example, as those commonly kept as house pets including, by way of example but not of limitation, cats and dogs.

Turning now to the figures of the drawing, the styptic powder-containing and nail-receiving article of the invention, there designated by the general reference numeral 10, comprises a receptacle-like structure formed as a tubular body 12 and a cavity 14 defined in the body. Tubular body 12 has a continuous, circumferential side wall 16 which extends from a top surface 18 to a bottom surface or base 20 upon which article 10 may conveniently and supportedly rest during periods of non-use and/or use. Body 12 has a predetermined height H between its top and bottom surfaces 18, 20, the height H being primarily a matter of design choice as will hereinafter become clear. Those skilled in the art will also readily recognize and appreciate that the exterior configuration of body 12 may take on any of a wide variety of forms other than the generally tubular, cross-sectionally round configuration of the embodiment herein disclosed.

Cavity 14 extends substantially vertically downward into the interior of body 12 from its top surface 18. The cavity is defined by a peripheral side wall 22 and a bottom generally designated 24 and, in the preferred embodiment, has the specific configuration best seen in FIG. 2. As there shown, peripheral side wall 22 extends downward from body top wall 18 to an extent E and, from there, extends gradually downward along sloping surface 26 to a generally centrally-located depression 28. The distance from body top wall 18 to depression 28 defines the predetermined depth D to which, as will hereinafter become clear, a dog's nail is intended to be inserted into cavity 14 in the contemplated use of the inventive article 10.

Figure 2:
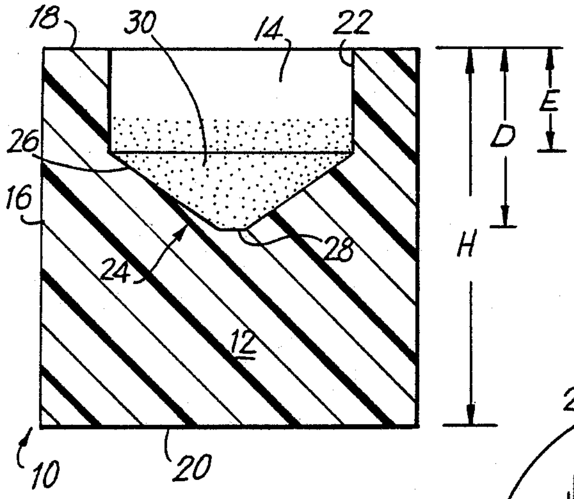
FIG. 2 is a sectional view taken along the lines II—II in FIG. 1.
Figure 3:
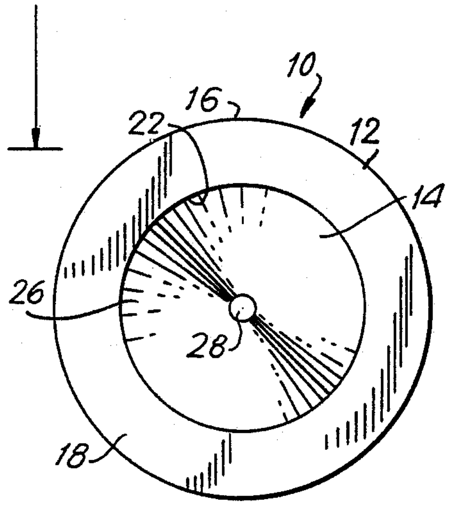
FIG. 3 is a top plan view of the article illustrated in FIG. 1.

In use, a quantity of styptic powder 30, depicted by the stippling seen in FIG. 2, is placed into cavity 14 in an amount appropriate for applying the styptic material to a dog's nail. In general, a sufficient quantity of styptic powder for substantially filling cavity 14 may be introduced into the cavity and thereafter replenished only when repeated use of the inventive article requires the addition of more styptic powder into the cavity so as to properly coat a dog's nail.

When in the course of a manicure the dog's nail begins to bleed, the nail is simply inserted into cavity 14 until the nail end is brought into substantial abutment with depression 28 of cavity bottom 24. In so doing, it should be noted that the illustrated, and presently preferred, configuration of cavity bottom 24 facilitates entry of the nail into the cavity to its intended and desired depth without the need to visually observe the depth to which the nail has been inserted. More particularly, this facilitated entry of the nail to the appropriate depth is effected by sloping surface 26 which may automatically guide a nail end contacting surface 26 toward and into substantial abutment with depression 28. The predetermined depth D of depression 28 is especially selected so that the insertion of the dog's nail, until the nail end substantially abuts or contacts depression 28, automatically provides for sufficient coating of the nail with styptic powder 30 to facilitate the cessation of bleeding from the nail end.

Those skilled in the art will appreciate that insertion of the dog's nail into cavity 14 may be carried out by moving the dog's paw, and thereby the nail, into the cavity 14 of a relatively stationarily-disposed article 10, or by movement of article 10 into proximity with the relatively stationary dog's paw, or by a combined motion of both the dog's paw and article 10. The precise manner in which this operation is carried out will be at least partly dependent on the demeanor of the dog and the preferences and experience of the handler and/or manicurist, and all such variations are within the contemplated usage of the invention.

It should especially be understood and appreciated that by confining the styptic powder to the relatively enclosed area of cavity 14, the unintended and undesirable spreading and splattering of styptic powder into the air and onto the dog's paws and other body portions and coat is cleverly and reliably avoided so that the styptic powder is applied only where desired—i.e., onto the bleeding nail. Moreover, the provision in the disclosed embodiment of a depression 28—located at the predetermined depth D which corresponds to the maximum extension of cavity 14—assures ready and reliable application of the styptic powder to onlv the nail—indeed if desired to only a portion of the nail—and not to the paw or coat or other body portions of the animal is assured. The several noteworthy advantages achieved through usage of the article 10 of the present invention have not heretofore been available in a single unit to those manicuring a dog's nails in the course of grooming the animal.

While there have been shown and pointed out fundamental novel features of the invention as applied to a preferred embodiment thereof, it will be understood that various omissions and substitutions and changes in the form and details of the device illustrated and in its operation may be made by those skilled in the art without departing from the spirit of the invention. For example, as previously noted the general configuration of body 12—including its relative height, general outward appearance and cross-sectional shape—may be varied, primarily as a matter of design choice. Similarly, the cross-section of cavity 14 need not be round, and need not even follow or conform in shape to the periphery of body 12 but may, instead, assume any ornamental or otherwise appropriate configuration. Indeed, although cavity 14 has been illustrated in the disclosure as extending substantially vertically downward from top surface 14 along a generally straight-line path, the cavity may alternately follow a curved or angularly varied path by which a dog's nail inserted into the cavity is more readily or directly guided to the predetermined depth D. Moreover, although the particular configuration of bottom 24 illustrated in FIG. 2 is currently preferred, cavity bottom 24 may assume any shape, including in its most basic form a substantially straight bottom of constant depth D, so long as the predetermined depth D is less than the height H of body 12 at least as great as the minimum extension E of the cavity from receptacle top wall 18. Put another way, predetermined depth D should be the maximum depth to which any portion of the cavity bottom 24 extends into body 12 from its top wall 18.

These and numerous other modifications of the preferred embodiment herein disclosed are intended to be within the scope and contemplation of the invention. It is the intention, therefore, to be limited only as indicated by the scope of the claims appended hereto.

What is claimed is:

1. An article for facilitating the cessation of bleeding from the nails of dogs during the manicuring of a dog's nails, comprising:

a receptacle of a predetermined height and having therein defined a cavity extending substantially vertically from a wall of said receptacle into the interior thereof to a cavity bottom;

said cavity having at least a portion of predetermined depth less than said predetermined height and no less than the minimum extension of said cavity from said wall top of the receptacle to said cavity bottom;

said predetermined depth substantially corresponding to the length of a dog's manicured nail; and a quantity of styptic powder disposed in said cavity in an amount such that, when the end of a dog's nail which has begun to bleed in the course of a manicure is placed into said cavity to the predetermined depth of said cavity portion, the nail end is sufficiently immersed is said styptic powder so as to properly coat the nail end with said powder and thereby facilitate the cessation of bleeding from the nail end, and said predetermined depth of the cavity portion being such as to enable the ready application of styptic powder to the nail while avoiding soiling of the paws and coat and other body portions of the dog with said styptic powder while controlling bleeding from the nail end.

2. An article in accordance with claim 1, wherein said cavity portion comprises a nail end receiving depression of predetermined depth greater than the extension of the remainder of said cavity from said wall of the receptacle.

3. An article in accordance with claim 2, said cavity bottom including a surface downwardly sloped and terminating at said depression for automatically directing a nail end into said cavity to substantial abutment with said depression and thereby immersing the nail end in said styptic powder to an appropriate depth for properly coating the nail end with said powder to facilitate the cessation of bleeding from the nail end without soiling of the paw and coat and other body portions of the dog with said styptic powder.

* * * * *

UNITED STATES PATENT AND TRADEMARK OFFICE
CERTIFICATE OF CORRECTION

PATENT NO. : 4,747,842

DATED : May 31, 1988

INVENTOR(S) : DAVID DIETZ

It is certified that error appears in the above-identified patent and that said Letters Patent is hereby corrected as shown below:

Column 4, line 63, delete "is" and substitute --in--.

Signed and Sealed this

Twenty-first Day of February, 1989

*Attest:*

DONALD J. QUIGG

*Attesting Officer* *Commissioner of Patents and Trademarks*